(12) United States Patent
Smith et al.

(10) Patent No.: US 9,415,149 B2
(45) Date of Patent: *Aug. 16, 2016

(54) METHOD AND SYSTEM FOR POWERING IMPLANTABLE DEVICES

(71) Applicant: University of Washington through its Center for Commercialization, Seattle, WA (US)

(72) Inventors: Joshua R. Smith, Seattle, WA (US); Pramod Bonde, New Haven, CT (US); Benjamin H. Waters, Kirkland, WA (US); Alanson P. Sample, Hillsboro, OR (US)

(73) Assignee: Yale University, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/481,569

(22) Filed: Sep. 9, 2014

(65) Prior Publication Data

US 2014/0378743 A1    Dec. 25, 2014

Related U.S. Application Data

(63) Continuation of application No. 13/843,884, filed on Mar. 15, 2013, now Pat. No. 8,827,889.

(60) Provisional application No. 61/734,236, filed on Dec. 6, 2012, provisional application No. 61/691,127, filed on Aug. 20, 2012, provisional application No. 61/649,496, filed on May 21, 2012.

(51) Int. Cl.
*A61N 1/362* (2006.01)
*A61M 1/12* (2006.01)
*A61M 1/10* (2006.01)

(52) U.S. Cl.
CPC .............. *A61M 1/127* (2013.01); *A61M 1/1086* (2013.01); *A61M 1/122* (2014.02);
(Continued)

(58) Field of Classification Search
CPC ... A61M 1/1086; A61M 1/122; A61M 1/127; A61M 2205/04; A61M 2205/3515; A61M 2205/3523; A61M 2205/3561
See application file for complete search history.

(56) References Cited

U.S. PATENT DOCUMENTS

| 3,553,736 A | 1/1971 | Kantrowitz et al. |
| 5,290,227 A | 3/1994 | Pasque |

(Continued)

FOREIGN PATENT DOCUMENTS

| WO | 2011/146661 A2 | 11/2011 |
| WO | 2013/177205 A1 | 11/2013 |

OTHER PUBLICATIONS

Allen et al., "Quality of life and functional status in patients surviving 12 months after left ventricular assist device implantation," *J Heart Lung Transplant*, 2010, 29:279-285.

(Continued)

*Primary Examiner* — George Manuel
(74) *Attorney, Agent, or Firm* — Riverside Law LLP (57) ABSTRACT

A ventricular assist device (VAD) system includes one or more external subsystems including an amplifier energizing a drive loop with alternating current, and a Tx resonator inductively coupled to the drive loop. An implanted subsystem includes a VAD, an Rx resonator that forms a magnetically coupled resonator with the Tx resonator, and a load loop for providing power to the VAD that is inductively coupled to the Rx resonator. A sensor monitors the drive loop and a controller uses the sensor data to adjust a system parameter to optimize energy transfer performance. Distributing a plurality of the external subsystems throughout a defined space provides a patient with freedom of movement within the defined space.

18 Claims, 7 Drawing Sheets

(52) U.S. Cl.
CPC ... *A61M 2205/04* (2013.01); *A61M 2205/3515* (2013.01); *A61M 2205/3523* (2013.01); *A61M 2205/3561* (2013.01)

(56) References Cited

U.S. PATENT DOCUMENTS

| | | | |
|---|---|---|---|
| 5,630,836 A | 5/1997 | Prem et al. | |
| 5,980,448 A | 11/1999 | Heilman et al. | |
| 6,331,744 B1 | 12/2001 | Chen et al. | |
| 6,445,956 B1 | 9/2002 | Laird et al. | |
| 6,764,373 B1 | 7/2004 | Osawa et al. | |
| 6,894,456 B2 | 5/2005 | Tsukamoto et al. | |
| 7,616,997 B2 | 11/2009 | Kieval et al. | |
| 7,986,122 B2 | 7/2011 | Fornage et al. | |
| 8,076,801 B2 | 12/2011 | Karalis | |
| 8,143,746 B2 | 3/2012 | Marzetta et al. | |
| 8,299,652 B2 | 10/2012 | Sample et al. | |
| 8,446,045 B2 | 5/2013 | Smith et al. | |
| 8,551,163 B2 | 10/2013 | Aber et al. | |
| 8,618,766 B2 | 12/2013 | Anderson et al. | |
| 8,767,871 B2 | 7/2014 | Park et al. | |
| 2003/0032853 A1 | 2/2003 | Korakianitis et al. | |
| 2004/0116769 A1 | 6/2004 | Jassawalla et al. | |
| 2005/0085683 A1 | 4/2005 | Bolling et al. | |
| 2010/0030304 A1 | 2/2010 | Haubrich | |
| 2010/0045114 A1 | 2/2010 | Sample et al. | |
| 2010/0052811 A1 | 3/2010 | Smith | |
| 2010/0063347 A1* | 3/2010 | Yomtov et al. | 600/17 |
| 2010/0081379 A1 | 4/2010 | Cooper et al. | |
| 2010/0182216 A1 | 7/2010 | Schmidhammer | |
| 2010/0187913 A1 | 7/2010 | Smith | |
| 2011/0140544 A1 | 6/2011 | Karalis et al. | |
| 2011/0156493 A1 | 6/2011 | Bennett | |
| 2011/0201870 A1 | 8/2011 | Forsell | |
| 2011/0241440 A1 | 10/2011 | Sakoda et al. | |
| 2011/0304408 A1 | 12/2011 | McKinzie, III | |
| 2012/0007690 A1 | 1/2012 | van Bezooijen | |
| 2012/0049648 A1 | 3/2012 | Choi et al. | |
| 2012/0080957 A1 | 4/2012 | Cooper et al. | |
| 2012/0153738 A1 | 6/2012 | Karalis | |
| 2012/0235636 A1 | 9/2012 | Partovi | |
| 2012/0243579 A1 | 9/2012 | Premakanthan et al. | |
| 2012/0248888 A1 | 10/2012 | Kesler | |
| 2013/0278209 A1 | 10/2013 | Von Novak, III | |
| 2013/0310630 A1 | 11/2013 | Smith et al. | |
| 2014/0015328 A1 | 1/2014 | Beaver et al. | |
| 2014/0070623 A1 | 3/2014 | Keeling et al. | |
| 2014/0073838 A1 | 3/2014 | Dague et al. | |
| 2015/0280444 A1 | 10/2015 | Smith et al. | |

OTHER PUBLICATIONS

Bonde et al., "Wireless Power for Ventricular Assist Devices: Innovation with the Free-Range Resonant Electrical Energy Delivery System (Free-D) for Mechanical Circulatory Assist," *AATS Annual Meeting 2013*, retrieved online—http://aats.org/annualmeeting/Abstracts/2011/T7.cgi.
Brown, "The History of Power Transmission by Radio Waves," *IEEE Transactions on Microwave Theory and Techniques*, 1984, MTT-32(9):1230-1242.
Cannon et al., "Magnetic Resonant Coupling as a Potential Means for Wireless Power Transfer to Multiple Small Receivers," *IEEE Transactions on Power Electronics*, 2009, 24(7):1819-1825.
Casanova et al., "A Loosely Coupled Planar Wireless Power System for Multiple Receivers," *IEEE Transactions on Industrial Electronics*, 2009, 56(8):3060-3068.
Christ et al., "Numerical Electromagnetic Analysis of Human Exposure for Wireless Power Transfer Systems," *Proceedings of the Tenth International Congress of the European Bioelectromagnetics Association (EBEA 2011)*, Feb. 21-24, 2011.
Deng et al., "Mechanical Circulatory Support Device Database of the International Society for Heart and Lung Transplantation: First Annual Report—2003," *J Heart Lung Transplant*, 2003, 22:653-662.
El-Banayosy et al., "Preliminary Experience with the LionHeart Left Ventricular Assist Device in Patients with End-Stage Heart Failure," *Ann Thorac Surg*, 2003, 75:1469-1475.
Frickey, "Conversions Between S, Z, Y, h, ABCD, and T Parameters which are Valid for Complex Source and Load Impedances," *IEEE Transactions on Microwave Theory and Techniques*, 1994, 42(2):205-211.
Gordon et al., "Ventricular assist device-related infections," *Lancet Infec Dis*, 2006, 6:426-437.
Haj-Yahia et al., "Midterm experience with the Jarvik 2000 axial flow left ventricular assist device," *J Thorac Cardiovasc Surg*, 2007, 134:199-203.
Holman et al., "Device Related Infections: Are We Making Progress?," *J Card Surg*, 2010, 25:478-483.
Imura, "Study on Maximum Air-gap and Efficiency of Magnetic Resonant Coupling for Wireless Power Transfer Using Equivalent Circuit," *IEEE International Symposium on Industrial Electronics*, 2010, pp. 3664-3669.
Kim et al., "Adaptive frequency with power-level tracking system for efficient magnetic resonance wireless power transfer," *Electronics Letters*, 2012, 48(8):1-2.
Kurs et al., "Wireless Power Transfer via Strongly Coupled Magnetic Resonances," *Science*, 2007, 317:83-86.
Low et al., "Design and Test of a High-Power High-Efficiency Loosely Coupled Planar Wireless Power Transfer System," *IEEE Transactions on Industrial Electronics*, 2009, 56(5):1801-1812.
Martin et al., "Effect of Body Mass Index and Device Type of Infection in Left Ventricular Assist Device Support Beyond 30 Days," *Interact Cardiovasc Thorac Surg*, 2010, 11(1): 20-30.
McSpadden et al., "Space Solar Power Programs and Microwave Wireless Power Transmission Technology," *IEEE Microwave Magazine*, 2002, 3(4):46-57.
Miller et al., "Use of a Continuous-Flow Device in Patients Awaiting Heart Transplantation," *N Engl J Med*, 2007, 357:885-896.
Mizannojehdehi et al., "Design and Analysis of A Class-E Frequency-Controlled Transcutaneous Energy Transfer System," *IEEE Conference on Electronics, Circuits and Systems*, 2006, pp. 21-24.
Monkowski et al., "Infections associated with ventricular assist devices: epidemiology and effect on prognosis after transplantation," *Transpl Infect Dis*, 2007, 9:114-120.
Ozeki et al., "Functions for Detecting Malposition of Transcutaneous Energy Transmission Coils," *ASAIO Journal*, 2003, 49:469-474.
Pagani et al., "Extended Mechanical Circulatory Support With a Continuous-Flow Rotary Left Ventricular Assist Device," *Journal of the American College of Cardiology*, 2009, 54(4):312-321.
Park et al., "Investigation of Adaptive Matching Methods for Near-Field Wireless Power Transfer," *IEEE Transactions on Antennas and Propagation*, (Impact Factor: 2.33), 2011, pp. 1769-1773.
Park et al., "Optimum Frequency of High Q-factor Resonator for Magnetic Resonance Coupling," *Microwave Conference (EuMC)*, 2011, pp. 61-63.
Raval et al., "A Wireless Power Transfer System for Low Power Electronics Charging Applications," *6th IEEE Conference on Industrial Electronics and Applications (ICIEA)*, 2011, pp. 520-525.
Raymond et al., "Obesity and Left Ventricular Assist Device Driveline Exit Site Infection," *ASAIO Journal*, 2010, 56:57-60.
Sample et al., "Experimental Results with two Wireless Power Transfer Systems," *IEEE Radio and Wireless Symposium*, 2009, pp. 16-18.
Sample et al., "Analysis, Experimental Results, and Range Adaptation of Magnetically Coupled Resonators for Wireless Power Transfer," *IEEE Transactions on Industrial Electronics*, 2011, 58(2):544-554.
Sample et al., "Enabling Seamless Wireless Power Delivery in Dynamic Environments," *Proceedings of the IEEE*, 2013, 101(6):1343-1358.
Smith et al., "Innovative Free-Range Resonant Electrical Energy Delivery System (Free-D System) for a Ventricular Assist Device Using Wireless Power," *ASAIO J.*, 2014, 60(1):31-37 (Abstract only).
Sun et al., "Design method for impedance matching networks," *IEEE Proc.-Circuits Devices Syst.*, 1996, 143(3):186-194.
Thompson et al., "Determination of the Impedance Matching Domain of Impedance Matching Networks," *IEEE Transactions on Circuits and Systems—I: Regular Papers*, 2004, 51(10):2098-2106.

(56) References Cited

OTHER PUBLICATIONS

Topkara et al., "Infectious Complications in Patients With Left Ventricular Assist Device: Etiology and Outcomes in the Continuous-Flow Era," *Ann Thorac Surg*, 2010, 90:1270-1277.
Waters et al., "Powering a Ventricular Assist Device (VAD) With the Free-Range Resonant Electrical Energy Delivery (FREE-D) System," *Proceedings of the IEEE*, 2012, 100(1):138-149.
Waters et al., "Adaptive Impedance Matching for Magnetically Coupled Resonators," *PIERS Proceedings*, Moscow, Russia, 2012, pp. 694-701.
Wilson et al., "Prevention of infective endocarditis: Guidelines from the American Heart Association," *JADA*, 2008, 139:3S-24S.
Zierer et al., "Late-Onset Driveline Infections: The Achilles' Heel of Prolonged Left Ventricular Assist Device Support," *Ann Thorac Surg*, 2007, 84:515-521.
DJ Goldstein et al. (Apr. 2011) "7 Driveline Infections in LVADs: Is it the Pump or the Patient?" Journal of Heart and Lung Transplantation, 30(4 Suppl):S10.
PA Heidenreich et al. (May 2013) "Forecasting the impact of heart failure in the United States: a policy statement from the American Heart Association," Circulation: Heart Failure, 6(3):606-619.
VL Roger et al. (Jan. 2012) "Heart disease and stroke statistics—2012 update: a report from the American Heart Association," Circulation, 125(1):e2-e220.
J. Stehlik et al. (Oct. 2010) "The Registry of the International Society for Heart and Lung Transplantation: twenty-seventh official adult heart transplant report—2010," Journal of Heart and Lung Transplantation, 29(10):1089-1103.
K. Sivaratnam and JM Duggan (Jan.-Feb. 2002) "Left ventricular assist device infections: three case reports and a review of the literature," ASAIO Journal, 48(1):2-7.
D. Simon et al. (Apr. 2005) "Left ventricular assist device-related infection: treatment and outcome," Clinical Infectious Diseases, 40(8):1108-1115.
MS Slaughter et al. (Dec. 2009) "Advanced heart failure treated with continuous-flow left ventricular assist device," New England Journal of Medicine, 361(23):2241-2251.
International Search Report and Written Opinion (ISR/WO) dated Oct. 23, 2015 for PCT/US2015/042941 filed Jul. 30, 2015.
ZT Demirozu et al. (Aug. 2011) "Arteriovenous malformation and gastrointestinal bleeding in patients with the HeartMate II left ventricular assist device," Journal of Heart and Lung Transplantation, 30(8):849-853.
S. Crow et al. (Jan. 2009) "Gastrointestinal bleeding rates in recipients of nonpulsatile and pulsatile left ventricular assist devices," Journal of Thoracic and Cardiovascular Surgery, 137(1):208-215.
EJ Birks et al. (Nov. 2006) "Left ventricular assist device and drug therapy for the reversal of heart failure," New England Journal of Medicine, 355(18):1873-1884.
YY Li et al. (Sep. 2001) "Downregulation of matrix metalloproteinases and reduction in collagen damage in the failing human heart after support with left ventricular assist devices," Circulation, 104(10):1147-1152.
O. Amir et al. (Apr. 2006) "Peripheral vascular reactivity in patients with pulsatile vs axial flow left ventricular assist device support," Journal of Heart and Lung Transplantation, 25(4):391-394.
S. Westaby et al., (Feb. 2007) "Circulatory support with attenuated pulse pressure alters human aortic wall morphology," Journal of Thoracic and Cardiovascular Surgery, 133(2):575-576.
T. Pirbodaghi et al. (Mar. 2014) "Physiologic and hematologic concerns of rotary blood pumps: what needs to be improved?" Heart Failure Reviews, 19(2):259-266.
J. Cowger et al. (Nov. 2010) "The development of aortic insufficiency in left ventricular assist device-supported patients," Circulation: Heart Failure, 3(6):668-674.
T. Pirbodaghi et al. (Feb. 2013) "Asymmetric speed modulation of a rotary blood pump affects ventricular unloading," European Journal of Cardio-Thoracic Surgery, 43(2):383-388.
NH Bishopric (Jun. 2005) "Evolution of the heart from bacteria to man," Annals of the New York Academy of Sciences, 1047:13-29.
T. Akimoto et al. (Aug. 1999) "Rotary blood pump flow spontaneously increases during exercise under constant pump speed: results of a chronic study," Artificial Organs, 23(8):797-801.
SM Parnis et al. (Sep.-Oct. 1997) "Progress in the development of a transcutaneously powered axial flow blood pump ventricular assist system," ASAIO Journal, 43(5):M576-M580.
T. Waters et al. (Jun. 1999) "Motor feedback physiological control for a continuous flow ventricular assist device," Artificial Organs, 23(6):480-486.
Choi et at (May 2001) "A Sensorless Approach to Control of a Turbodynamic Left Ventricular Assist System," IEEE Transactions on Control Systems Technology, 9(3):473-482.
JR Boston et al. (Jun. 2000) "Control issues in rotary heart assist devices," in Proceedings of the 2000 American Control Conference, 5:3473-7.
M. Yoshizawa et al. (Jul.-Aug. 2002) "Sensorless estimation of pressure head and flow of a continuous flow artificial heart based on input power and rotational speed," ASAIO Journal, 48(4):443-448.
PJ Ayre et al. (Aug. 2000) "Sensorless flow and head estimation in the VentrAssist rotary blood pump," Artificial Organs, 24(8):585-588.
T. Tsukiya et al. (May 1997) "Use of motor current in flow rate measurement for the magnetically suspended centrifugal blood pump," Artificial Organs, 21(5):396-401.
DM Karantonis et al. (Aug. 2007) "Noninvasive pulsatile flow estimation for an implantable rotary blood pump," 29th Annual International Conference of the IEEE Engineering in Medicine and Biology Society (EMBS 2007), pp. 1018-1021.
GA Giridharan and M. Skliar (Apr. 2006) "Physiological control of blood pumps using intrinsic pump parameters: a computer simulation study," Artificial Organs, 30(4):301-307.
International Search Report and Written Opinion (ISR/WO) dated Aug. 26, 2013 for PCT/US2013/042085 filed May 21, 2013.

* cited by examiner

METHOD AND SYSTEM FOR POWERING IMPLANTABLE DEVICES

CROSS-REFERENCES TO RELATED APPLICATIONS

The present application is a continuation application of U.S. patent application Ser. No. 13/843,884, filed Mar. 15, 2013, now U.S. Pat. No. 8,827,889, which claims benefit of priority under 35 U.S.C. §119(e) to U.S. Provisional Patent Application No. 61/649,496, filed May 21, 2012; U.S. Provisional Patent Application No. 61/691,127, filed Aug. 20, 2012; and U.S. Provisional Patent Application No. 61/734,236 filed Dec. 6, 2012, the contents of which are incorporated by reference herein in their entirety.

BACKGROUND

In recent decades, the fortuitous confluence of advances in medical and surgical capabilities, biomedical engineering, biocompatible materials development, and electronic and computer miniaturization has produced a revolution in the field of active implantable medical devices, with resultant increases in human longevity and quality of life. Examples of active implantable medical devices include artificial hearts, implantable heart monitors and defibrillators, pacemakers, neurostimulators, ventricular assist devices, and the like. One challenge associated with the use of such devices is providing a reliable source of energy to operate the device over a long period of time.

A ventricular assist device (VAD) is a medical device that partially or completely replaces the function of a damaged or failing heart. VADs typically assist the heart and do not completely take over cardiac function or require removal of the patient's heart. A particular VAD may be used to assist the patient's right ventricle (RVAD), left ventricle (LVAD), or both ventricles (BiVAD), depending on the needs of the patient. Although VADs may sometimes be intended for short term use, for example, to provide post-operative assistance to a surgically repaired heart or as a bridge while awaiting a transplant, increasingly VADs provide a long-term solution, for example, for patients suffering from congestive heart failure and for destination therapy.

The first generation VADs were approved for use in the United States by the Food and Drug Administration in 1994. A conventional VAD pump requires a percutaneous driveline, wherein a biocompatible cable extends through the patient's body to connect the VAD to a power source and system controller.

A trans-dermal driveline has many disadvantages and negative quality-of-life impacts for a patient. Moreover, due to improvements in VAD technology and the increasingly long-term use of VADs, the most common cause of complications requiring patient hospitalization and/or affecting patient mortality is no longer failure of the VAD itself. Rather the most common complications result from exit site infection (ESI) associated with the percutaneous driveline. ESI can result in repeated hospitalization, increased patient pain and suffering, and significant medical expenses incurred. Even reasonable precautions to reduce the risk of ESI can interfere with the patient's quality of life. The risk of ESI largely results from the need to continuously provide power through the protective barrier provided by the patient's skin to the implanted medical device for long-term operation of the device. It would be advantageous to provide power wirelessly to an implanted medical device such as a VAD.

Prior attempts to transfer power wirelessly through a patient's skin use conventional inductive coupling techniques, e.g., coils on the inner and outer surfaces of the skin. However, conventional inductive coupling energy transfer has several drawbacks. The need for very close separation distance between the coils, and restrictions on misalignment between the transmitting and receiving coils limit the practicality of conventional inductive coupling. The proximity limitation requires that the receiving coil be implanted just under the skin and the external transmitting coil be secured in a fixed position on the skin surface. Misalignment or excessive separation between the coils may cause the transmitter to increase the power supplied to accommodate the reduced efficiency. This effect may cause skin irritation and/or thermal injury from the increase in coil temperature due to greater power transmission, which can then lead to infections.

Some of the present inventors disclose wirelessly powered speakers using magnetically coupled resonators in Patent Application Pub. No. US 2010/0081379, to Cooper et al., which is hereby incorporated by reference in its entirety.

There is a need for improved methods and systems for providing power to active implanted medical devices.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A ventricular assist device (VAD) system provides relatively long distance wireless power transmission to the VAD, includes an external subsystem, and an implanted subsystem. The external subsystem includes an amplifier or controllable AC power supply that is operably connected to a drive loop, to provide RF energy to the drive loop. A sensor, such as a directional coupler, vector network analyzer, or the like, provides information from the drive loop. The implantable subsystem includes the VAD, a load loop operably connected to provide energy to the VAD, and a receiver resonator that is inductively coupled to the load loop. During operation, the transmitter resonator and the receiver resonator form a magnetically coupled resonator (MCR), such that the VAD is energized from RF energy from the amplifier that is inductively transmitted from the drive loop to the MCR, and is inductively transmitted from the MRC to the load loop. A controller is operable to receive data from the sensor, and to control an operating parameter to optimize the energy transfer efficiency in the MCR.

In an embodiment of the VAD system, the MCR is effective to transfer energy over distances exceeding one meter.

In an embodiment, the VAD system further comprises a relay resonator configured to be worn by the patient. For example, the transmitter resonator, transfer resonator, and receiver resonator may define an MCR. In an embodiment, the transfer resonator is disposed in a garment that is configured to position the relay resonator over the implanted receiver resonator.

In an embodiment, the external subsystem includes a plurality of subsystems that are distributed in a defined space, wherein the receiver resonator is configured to selectively receive energy from one or more of the external subsystems, for example the nearest external subsystem, providing the patient with freedom of movement within the defined space.

In an embodiment, a plurality of transfer resonators are also provided in the defined space, to facilitate energy transfer to the receiver resonator.

In an embodiment, the VAD system further comprises a portable energy system with an energy source and a portable transmitter resonator, wherein the portable energy system is operable to selectively couple the portable transmitter resonator with the receiver resonator.

In an embodiment, the controller actively controls the amplifier frequency to optimize energy transfer efficiency. In another system, the external subsystem comprises a matching network and the controller controls the matching network, for example a π-match network or an L-match network, to change the impedance of the system to optimize energy transfer efficiency. In an embodiment, the matching network is implemented using a switchable bank of capacitors.

In another aspect of the invention, a method for providing energy to an implanted device, for example a VAD, includes (i) providing a garment having a relay resonator that is positioned in the garment such that the relay resonator overlies the receiver resonator when the garment is worn by the patient; (ii) providing a plurality of external energy systems disposed throughout a defined space, wherein each of the plurality of external energy systems comprise a drive loop connected to an alternating current source and a transmitter resonator configured to form a magnetically coupled resonator (MCR) with the receiver resonator and the relay resonator, wherein the drive loop is inductively coupled to the transmitter resonator; and (iii) monitoring the drive loop with a sensor, for example a directional coupler, to generate data and using the data to adjust an impedance of the MCR.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
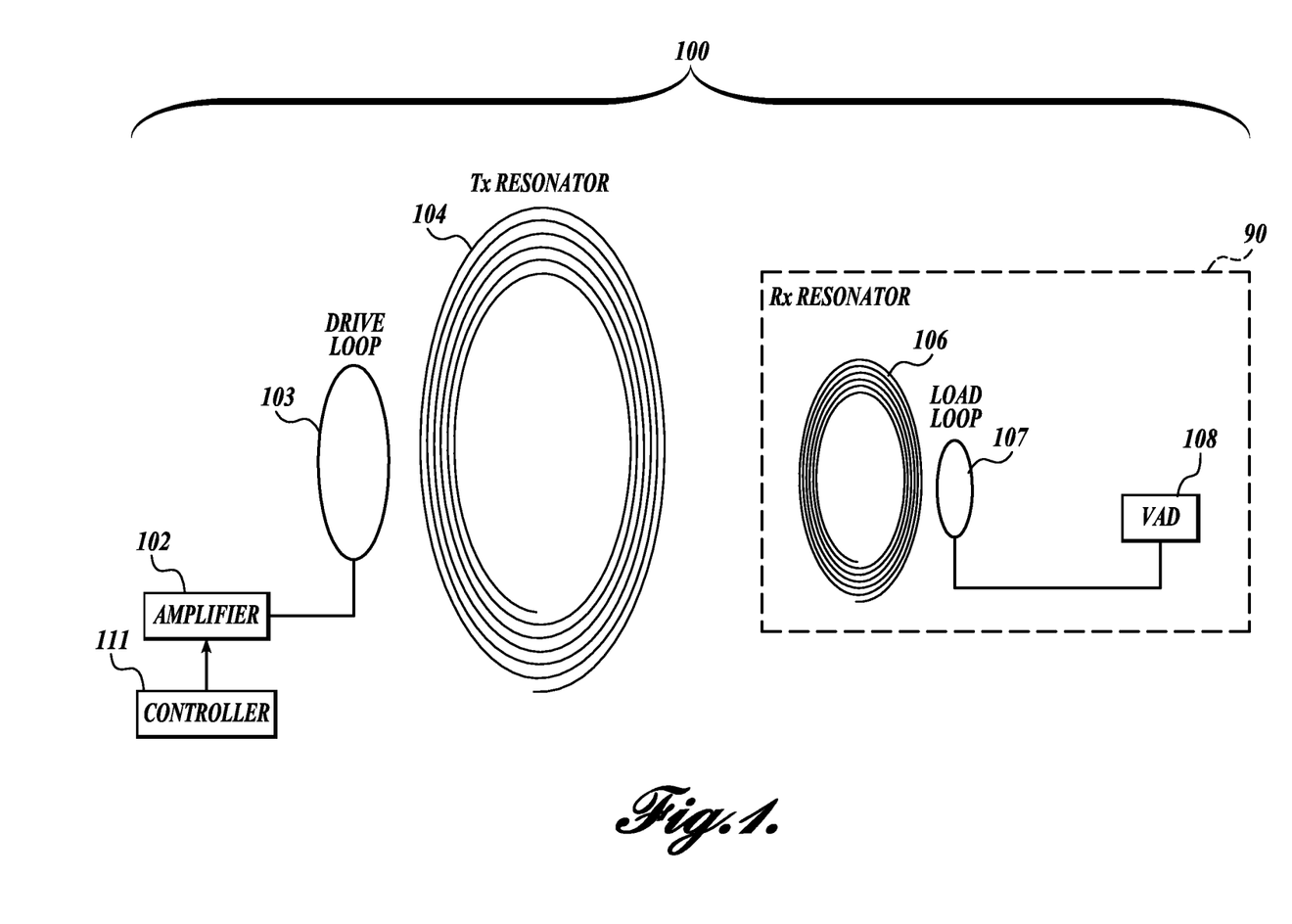
FIG. 1 is a schematic diagram of a first embodiment of an implantable medical device with an MCR coil wireless energy transfer system, in accordance with the present invention.

An embodiment of a system in accordance with the present invention will now be described with reference to the FIGURES, wherein like numbers indicate like parts. A schematic energy transfer system 100 in accordance with the present invention for a ventricular assist device (VAD) 108 is shown in FIG. 1. The energy transfer system 100 is sometimes referred to as a free-range resonant electrical delivery (FREE-D) system 100.

The energy transfer system 100 provides wireless power to a VAD 108 implanted in a patient 90. The system 100 uses strong resonant coupling between a high-Q transmitter resonator (Tx resonator) 104, and a resonantly coupled high-Q receiver resonator (Rx resonator) 106. The Tx resonator 104 and the Rx resonator 106 comprise a pair of magnetically coupled resonators (MCR) coils 104, 106. An amplifier 102 and drive loop 103 are inductively coupled to the Tx resonator 104, providing energy to the system 100. The Rx resonator 106 is inductively coupled to a load loop 107 providing electrical energy to the VAD 108.

The transmitter in this embodiment comprises the single-turn drive loop 103 and the multiturn Tx resonator 104. However, multiturn drive loops are also contemplated. References here to a drive loop or to a load loop are intended to encompass either single—or multiturn loops. The two-element receiver comprises the multiturn Rx resonator 106, which receives energy from the Tx resonator 104, and is inductively coupled to the load loop 107 to provide power to the VAD 108. The resonant systems efficiently exchange energy by sharing non-radiative magnetic fields that oscillate at a specified resonant frequency. The most significant interaction occurs between the high-Q inductor-capacitor-resistor (LCR) tank MCR coils 104, 106. These MCR coils 104, 106 share a mutual inductance $M_{ij}$ that is a function of resonator geometry, the separation distance and orientation of the MCR coils 104, 106, and the drive current. So long as the Rx resonator 106 is within range of the magnetic field, generated by the Tx resonator 104, power can be transferred wirelessly between them. As discussed below, the effective range may be extended, for example using transfer resonators, matching networks, and the like.

The controller 111 actively controls the output frequency of the amplifier 102 in order to maintain optimal energy transfer between the MCR coils 104, 106. The high-Q MCR coils 104, 106 may efficiently transfer power across distances on the order of one or more meters, and may be sized to accommodate application specifications, such as room size and patient body geometry. The MCR coils 104, 106 in one embodiment are configured to efficiently transfer power across distances of greater than one meter.

Unlike prior art inductively coupled systems, the present energy transfer system 100 uses dynamic power management control to maintain high energy transfer efficiency over relatively long distances wherein one or both of the MCR coils 104, 106 may be moving. For example, in one embodiment the controller 111 controls the frequency of the amplifier 102 to maintain energy transfer at a relatively high efficiency, adapting to variations in the separation distances and relative orientations of the MCR coils 104, 106. In another embodiment, the coupling between the high-Q MCR coils 104, 106 is actively controlled with one or more matching networks that are operable to adjust impedances in the system 100, such that high energy transfer efficiency can be achieved at a fixed frequency.

In an equivalent circuit for this system, in terms of conventional lumped circuit elements L, R, and C, the drive loop 103, Tx resonator 104, Rx resonator 106, and load loop 107 are modeled as inductors, referred to herein as L1, L2, L3, and L4, respectively. Corresponding capacitors C1, C2, C3, and C4 are selected such that the MRC coils 104, 106 will operate at the same resonant frequency according to:

$$f_{res} = \frac{1}{2\pi\sqrt{L_i C_i}} \quad (1)$$

Each of the three resonant circuits is linked by the corresponding coupling coefficients $k_{12}$, $k_{23}$, and $k_{34}$. The relationship between the coupling coefficient and the mutual inductance between each resonator is given by:

$$k_{ij} = \frac{M_{ij}}{\sqrt{L_i L_j}} \quad (2)$$

The transfer function may be derived using Kirchhoff's voltage law and flux linkages. The coupling coefficient between the Tx resonator 104 and the Rx resonator 106 is inversely proportional to the distance between the MCR coils 104, 106. As the separation distance increases, the amount of coupling between the resonators decreases. A frequency splitting of the two resonant peaks converges at $f_{res}$.

In the overcoupled regime, the MCR coils 104, 106 share substantial magnetic flux and the system is capable of achieving maximum efficiency. In the overcoupled regime there are two different resonant frequencies caused by the in-phase and out-of-phase modes of the overlapping magnetic fields, and a maximum efficiency can be maintained by operating at a frequency corresponding to the lower frequency peak which corresponds to the in-phase mode of the resonant system. If the coils 104, 106 are de-tuned or if the quality factor Q of a coil is significantly reduced, as will likely occur for an implanted coil due to the added parasitic resistance and capacitance from surrounding tissues, the frequency corresponding to the maximum efficiency may vary.

In the undercoupled regime, the shared flux falls below a threshold such that maximum efficiency cannot be achieved. Critical coupling is the point of transition between the overcoupled regime and the undercoupled regime, and corresponds to the greatest range at which maximum efficiency can be achieved. The undercoupled regime is capable of wireless energy transfer, but the maximum achievable efficiency falls significantly as the separation distance increases.

Figure 2:
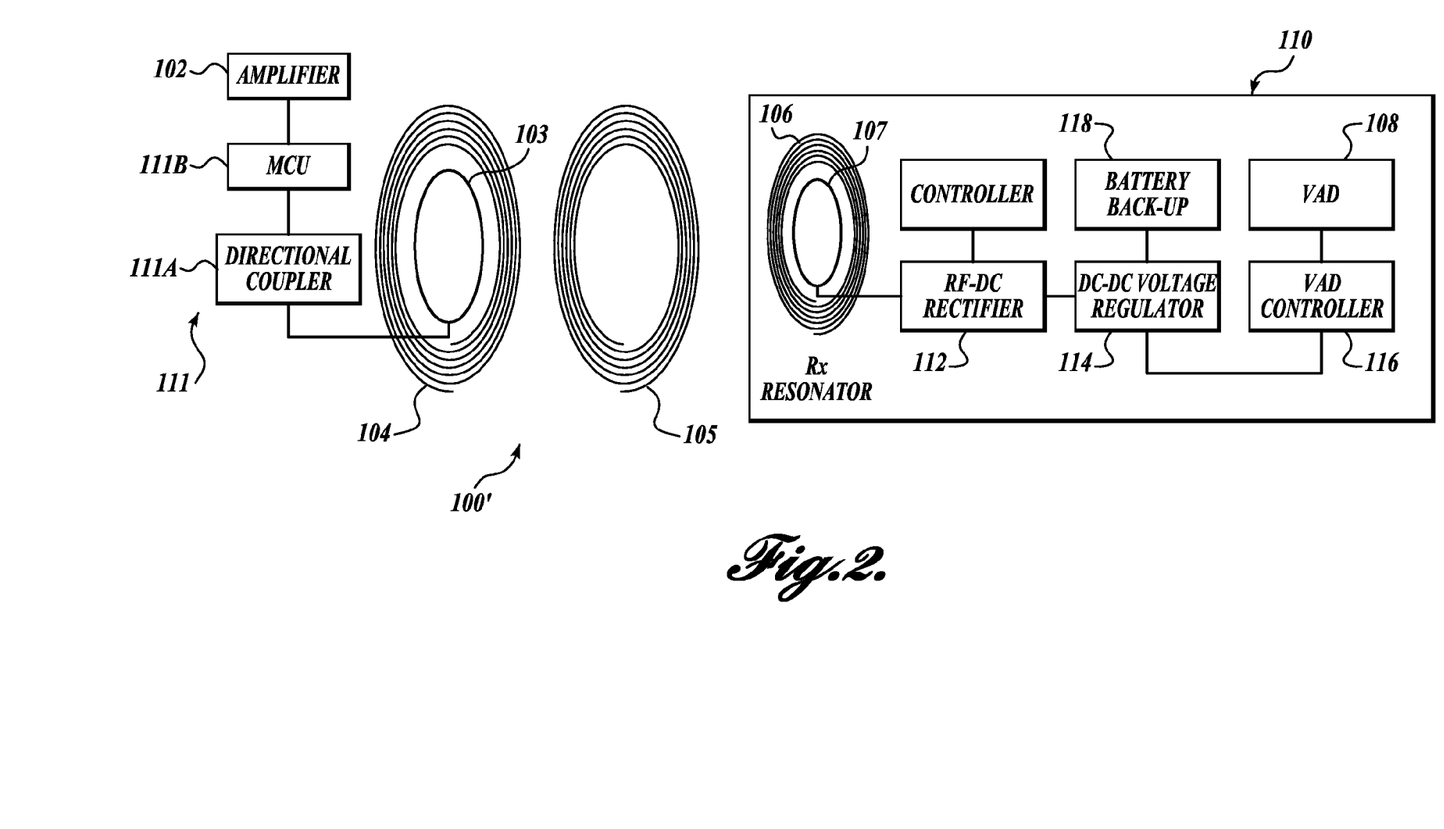
FIG. 2 is a schematic diagram of a second embodiment of an implantable medical device with an MCR coil wireless energy transfer system including a relay resonator, in accordance with the present invention.

FIG. 2 shows another embodiment of an energy transfer system 100' in accordance with the present invention, and illustrates power management control systems for both the transmission side and the receiver side of the system 100'. The system 100' includes the controller 111, drive loop 103, and Tx coil 104. A relay resonator 105 is positioned between the Tx resonator 104 and the Rx resonator 106 and is operable to improve the range of high-efficiency energy transfer to the Rx resonator 106. As used herein, the three-resonator system comprising the Tx resonator 104, one or more relay resonators 105, and the Rx resonator 106 is expressly defined to be an example of a magnetically coupled resonator. The three- (or more) resonator system is operable to cooperatively transmit energy between the Tx resonator 104 and the Rx resonator 106. A VAD implant device 110 is configured to be implantable in the patient. The device 110 receives energy from the Tx resonator 104 either directly or through the relay resonator 105.

In this embodiment, the transmitter controller 111 includes a directional coupler 111A, and a microcontroller unit (MCU) 111B that receives data from the directional coupler 111A and controls the power amplifier 102 to optimize energy transfer efficiency. The amplifier 102 delivers an RF signal through the directional coupler 111A to the drive loop 103. The directional coupler 111A measures the magnitude of the forward and reflected waves, which can be used to approximate the transmission power gain $S_{21}$ of the MCR coils 104, 106. The MCU 111B is configured to adjust the amplitude and/or frequency of the amplifier 102 such that the signal delivered to the Tx drive loop 103 approximately minimizes the reflected power, thereby maximizing energy transfer efficiency between the Tx MCR coil 104 and the Rx MCR coil 106.

At the receiver side, the implant 110 includes the Rx resonator 106, which may be significantly smaller than either the Tx resonator 104 or the relay resonator 105, and an RF-dc rectifier 112 that converts the RF signal to a direct current rectified voltage. A dc-dc voltage regulator 114 steps down this rectified voltage. In a current embodiment, the dc voltage is stepped down to 13.1 Vdc, which is compatible with the requirements of the VAD controller 116 and VADs 108 tested with the energy transfer system 100'. The regulated dc voltage is delivered to the VAD controller 116, which powers the VAD 108 and may also be configured to monitor conditions such as flow rate, pump speed, and pump power. A rechargeable backup battery 118 provides temporary power to the VAD controller 116 and VAD 108, as needed.

It is desirable to provide an energy transfer system that would permit the patient freedom of movement within their home or other building. However, although the energy transfer system 100 provides for efficient wireless energy transfer over a relatively long distance, it may not provide sufficient range to accommodate a desired range of movement.

Figure 3:
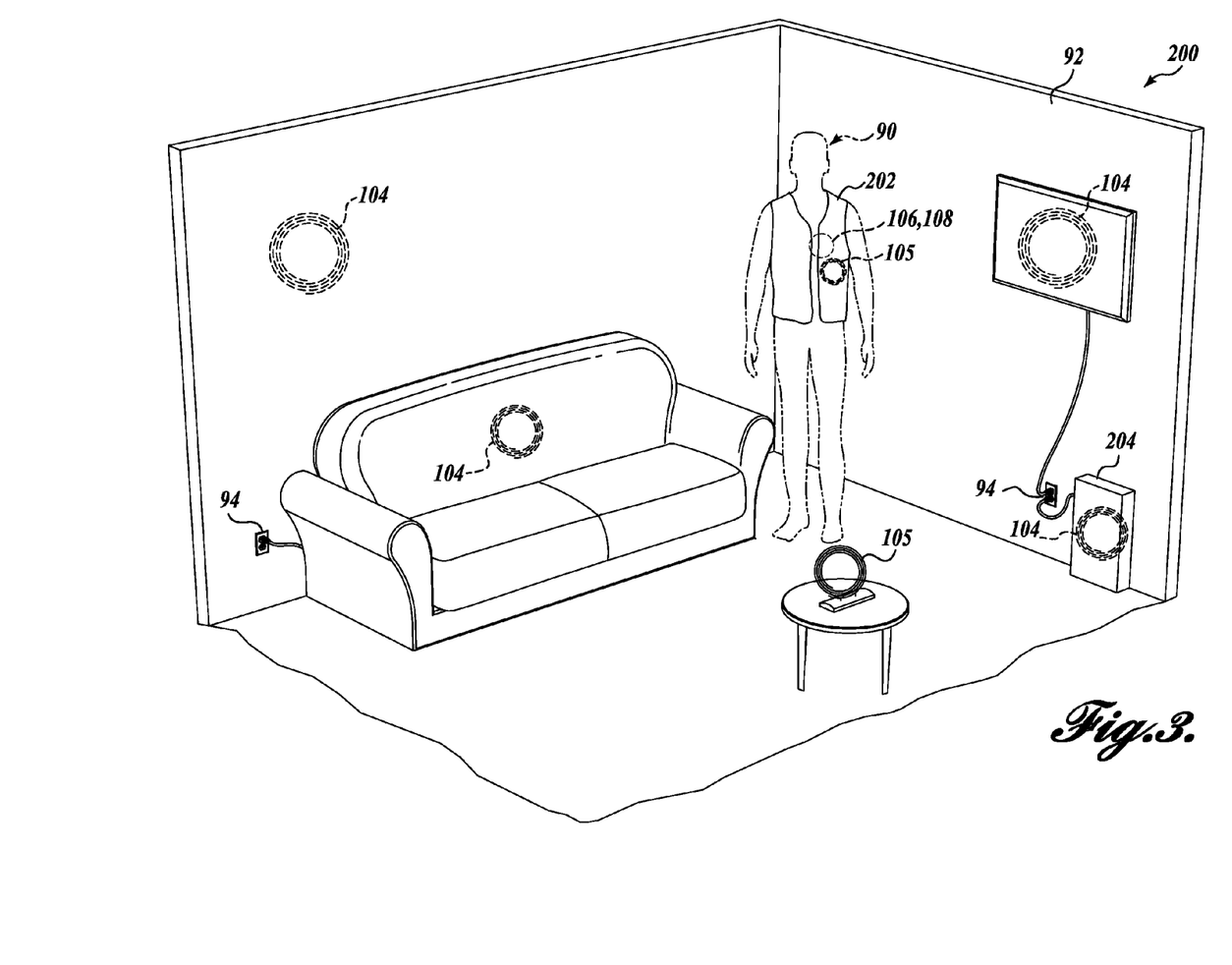
FIG. 3 is an environmental view showing the use of the embodiment shown in FIG. 2 configured with multiple transmitter systems to define a space for wirelessly transmitting power for an implanted medical device.

FIG. 3 illustrates an energy transfer system 200 in accordance with the present invention for wirelessly powering an implanted VAD 108 within a defined space. The system 200 in this embodiment includes a plurality of Tx resonators 104, each of which are inductively coupled to corresponding drive loops 103 and controllers 111 (not shown, for clarity). The Tx resonators 104 are disposed throughout the desired space 92. For example, in a household, one or more Tx resonators 104 may be hidden in furniture, walls, floors, couches, tables, art pieces, beds, and the like. One or more Tx resonators 104 may be mounted onto the wall or the ceiling, on free-standing platforms, or placed on an end table or other convenient surface. The Tx resonators 104 are located throughout the space such that energy can be efficiently and wirelessly transmitted to the patient's VAD 108 from anywhere in the space.

A relay resonator 105 is provided in a vest or other garment 202 that is worn by the patient 90. Preferably the relay resonator 105 and garment 202 are configured such that when the garment 202 is properly donned, the relay resonator 105 is secured near the portion of the patient's body directly over the implanted Rx resonator 106, thereby positioning the relay resonator 105 a fixed distance from the implanted Rx resonator 106 to ensure seamless energy transfer to the VAD 108. Typically the relay resonator 105 is larger than the implanted Rx resonator 106, and is operable to increase the working range of the wireless energy transfer. Alternatively, the wearable relay resonator 105 may be disposed in or on a different wearable device, for example a sash, shoulder belt, chest strap, pendant or the like.

It is contemplated, for example, that additional free-standing relay resonators 105 (one shown) may be disposed about the space 92, in order to improve the range of the energy transfer. For example, several Tx resonators 104 and the associated power management subsystem are installed in locations that have convenient access to electrical outlets 94.

Additional freestanding relay resonators 105 may be installed or positioned in central locations away from power sources. The relay resonators 105 provide intermediate resonant links to facilitate wireless energy transferred from the Tx resonators 104 to the relay resonator 105 worn by the patient.

Adding a relay resonator 105 to the MCR coils 104, 106 model introduces a third resonant mode to the system in the overcoupled regime. The third mode will be centered at the resonant frequency of the system. Adding additional relay resonators 105 will continue to increase the working range of the wireless energy transfer, although the maximum achievable efficiency will decrease, and the number of modes will continue to increase, as more relay resonators 105 are introduced to the system. The same basic power management and automatic tuning algorithms (e.g., frequency tuning, adaptive impedance matching, or the like) are capable of accommodating multiple-mode resonant systems.

The system 200 provides the patient with the ability to freely maneuver throughout their home or other space 90 untethered, while receiving wireless power from the nearest Tx resonator 104. Optionally, if the patient needs to leave the home, a portable battery system 204 with a Tx resonator 104 can be used to temporarily provide energy to the Rx resonator 106 through the relay resonator 105.

Unlike far-field antennas in which the input impedance of the antenna is constant, near-field antennas like the resonators 104, 105, 106 in the system 100' (FIG. 2) have strong electromagnetic field interaction, thus the input impedance of the resonators is constantly changing as a function of the mutual inductance between the resonators. For example, as the distance between the Tx resonator 104 and the Rx resonator 106 increases, the coupling coefficient between the multiturn resonators decreases because the mutual inductance decreases. The rectifier 112 on the receiver side also has a complex input impedance that is changing as a function of the input power and load conditions. As a result, the impedance looking into the Tx resonator 104 is constantly changing, making it difficult to design an impedance matching network.

As discussed above, one approach to optimizing the efficiency of the wireless energy transfer is to actively control the amplifier 102 frequency tuning to track the maximum energy transfer peaks. However, regulatory limitations may require operation of the energy transfer system over a relatively narrow frequency band. For example, it may be preferable to operate the energy transfer system within the Industrial, Scientific, and Medical (ISM) bands governed in the U.S. by Parts 15 and 18 of the Federal Communication Commission (FCC) rules.

As described in more detail below, a dynamic impedance matching network may be implemented to optimize enemy transfer to the device 110 at a single frequency within the ISM band.

A system and method for the wireless power transmission that take advantage of the unique properties of magnetically coupled resonators (MCRs) will now be described. A detailed description of the operating principles and performance characteristics of MCRs is presented in "Analysis, Experimental Results, and Range Adaptation of Magnetically Coupled Resonators for Wireless Power Transfer," A. Sample, D. Meyer, and J. Smith, *Industrial Electronics, IEEE Transactions on*, Vol. 58, No. 2, pp. 544-554, February 2011, which is hereby incorporated by reference in its entirety. A brief overview of system features that can enable seamless wireless power delivery is provided to facilitate an understanding of the present invention. The system uses high-Q magnetically coupled resonators, and one or more dynamic impedance matching networks to maintain high power transfer efficiency between the resonators within a very narrow frequency band, or at a single predetermined frequency.

The input impedance of the MCR wireless power system 100 shown in FIG. 1 will vary due to changes in the location and/or orientation of the resonators 104, 106 because the mutual inductance between the Tx resonator 104 and the Rx resonator 106 varies as a function of distance and orientation. Additionally, when the MCR coils 104, 106 are sufficiently close to each other, the cross coupling and direct capacitance feed through from one coil can detune the opposite coil and reduce the quality factor Q of each MCR. Also, an implanted resonator can have a reduced Q due to the added parasitic resistance and capacitive & tuning caused by surrounding tissues. All of these factors contribute to a mismatch between source and load impedance that substantially degrades power transfer efficiency.

Figure 4:
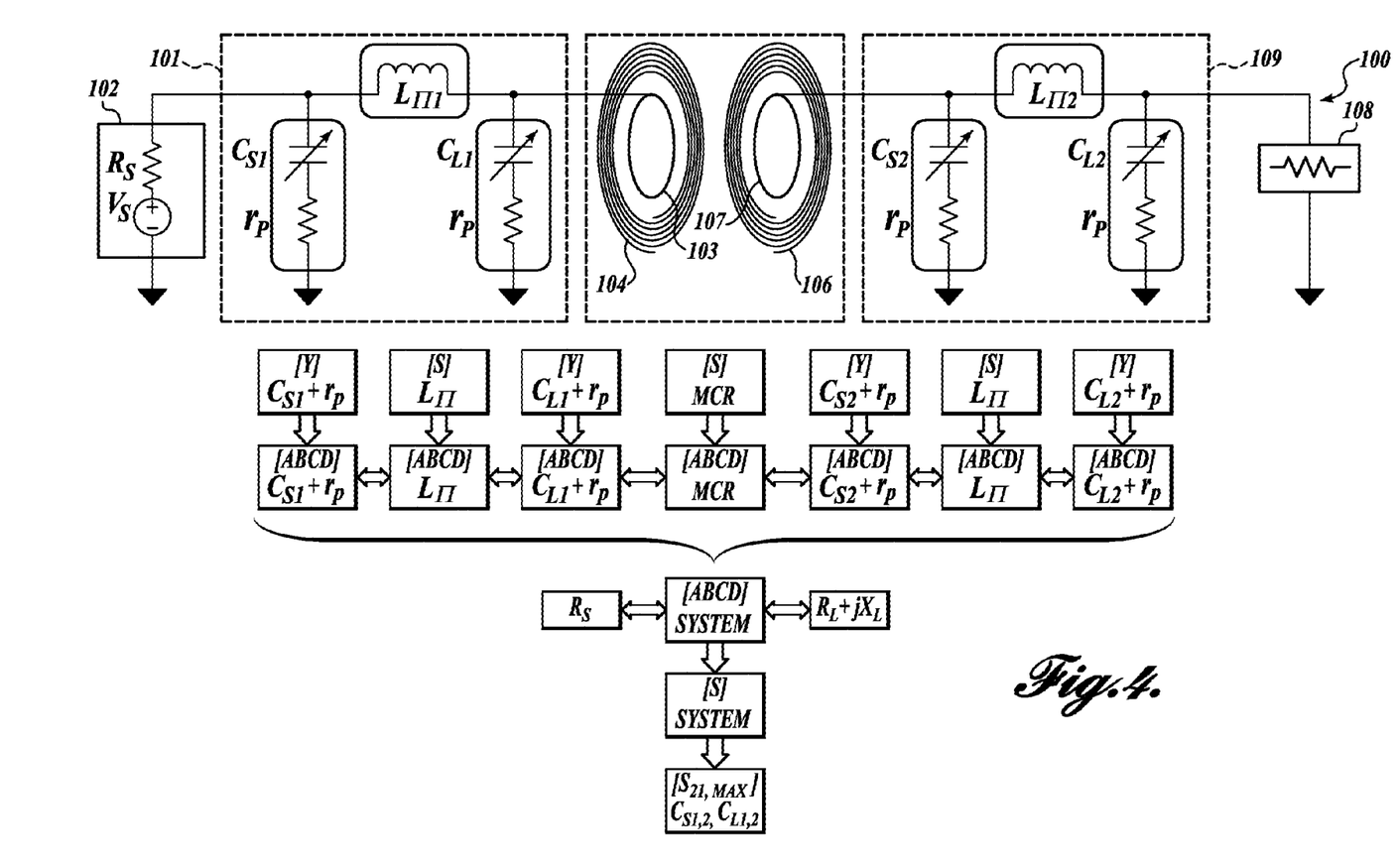
FIG. 4 illustrates a method for optimizing a wireless power system such as that shown in FIG. 1.

As described herein, high efficiency narrowband energy transfer may be achieved by adding dynamic impedance matching networks to one or both of the drive loop 103 and the load loop 107 or directly connecting them to one or both of the Tx resonator 104 or the Rx resonator 106. Referring to FIG. 4, a first adjustable π-match network 101 is provided between the amplifier 102 and the drive loop 103 that is inductively coupled to the Tx resonator 104. A second adjustable π-match network 109 is provided, between the load loop 107 coupled to the Rx resonator 106 and a VAD 108. In this embodiment, the topology includes variable capacitors $C_{S1}$, $C_{L1}$ and a fixed inductor $L_{\pi 1}$ (with the parasitic equivalent series resistance $r_p$) on the transmit side, and variable capacitors $C_{S2}$, $C_{L2}$ and a fixed inductor $L_{\pi 2}$ on the receive side.

This system 100 performs dynamic impedance matching by dynamically controlling the variable capacitances of both π-match networks 101, 109. Other matching networks, for example L-match networks, may alternatively be used and are contemplated by the present invention. However, compared to other matching network topologies, the π-match network is currently preferred for adaptive wireless power transfer. The π-match network has several advantages, for example it uses a fixed-value inductor in the high-current path, and variable capacitors that handle relatively low power in shunt configurations, and, it is able to match source impedances that are both greater than, equal to, and less than load impedances.

Although FIG. 4 shows matching networks on both the Tx side and the Rx side, it is also contemplated that a system may be implemented with a matching network on only one side. A π-match network 101 at the input to the drive loop 103 and a second π-match network 109 at the output from the load loop 107 provide a wider range of impedance matching between source and, load impedances, thus resulting in higher wireless power transfer efficiency at a single frequency for any separation distance. This is because in many instances π-match networks at both sides can do a better job of impedance matching when there is a large deviation between source and load termination impedances. A π-match network has an extra degree of freedom from the typical L-match network, and that is the Q factor of the matching network, which can be tuned to achieve a wideband or narrowband impedance match. In the L-match network, the Q factor of the matching network is fixed for a given impedance and capacitance. In a π-match network, the same impedance match can be achieved for a wide range of matching network Q factors.

A method has been developed, that uses unconstrained nonlinear optimization to determine the ideal capacitor values for π-match networks 101, 109 that will maximize the forward transmission gain, S21, for a range of coupling coefficients between the MCR coils 104, 106. The current algorithm measures one or more of the scattering parameters, or S-parameters ([S] matrices), for $L_\pi$ and for the set of MCR coils 104, 106, and converts the S-parameters into ABCD-matrices, as is known in the art for two-port network analysis. The ABCD representation is convenient because a series of cascaded two-port networks can be modeled by computing the product of their individual ABCD matrices to form a single lumped ABCD-matrix. The ABCD matrices for the Tx π-match network 101, the MCR coils 104, 106 and the Rx ππ-match network 109 are multiplied together. After converting the lumped ABCD-matrix back to an S-matrix, the source and load capacitor values in each π-match network 101, 109 are determined by selecting values that optimize |S21| at the desired frequency.

The method will now be described in more detail, and is illustrated for the system 100 in FIG. 4. The S-parameters for a set of MCRs are obtained. The S-parameters may be obtained, for example, from manufacturer data, with a vector network analyzer, with a directional coupler, or the like. It is preferable to use measured data so that all of the parasitic effects are considered. Typically, the transfer functions for a 4-coil MCR system neglect parasitic effects such as cross-coupling and coil de-tuning that can significantly reduce efficiency at the resonant frequency.

The admittance matrices [Y] are also defined for the capacitance components of the π-match networks 101, 109. The [S] and [Y] matrices are converted into [ABCD] transmission matrices. These [ABCD] matrices for the individual component are combined, e.g., by multiplying the cascaded [ABCD] matrices to define a system [ABCD] matrix. A system [S] matrix is calculated from the system [ABCD] matrix using complex termination impedances to match a source impedance to a defined load impedance. Finally, a conventional constrained non-linear optimization algorithm may be used to determine the component values $C_{S1}$, $C_{L1}$, $C_{S2}$, $C_{L2}$ in each network that maximize S21. Equivalently, the algorithm may minimize the reflection S-parameter, S11. It is also contemplated that the algorithm may be configured to maximize power transfer efficiency, if data from an out of band radio is available to communicate between the power transmit side and receive side.

Figure 5:
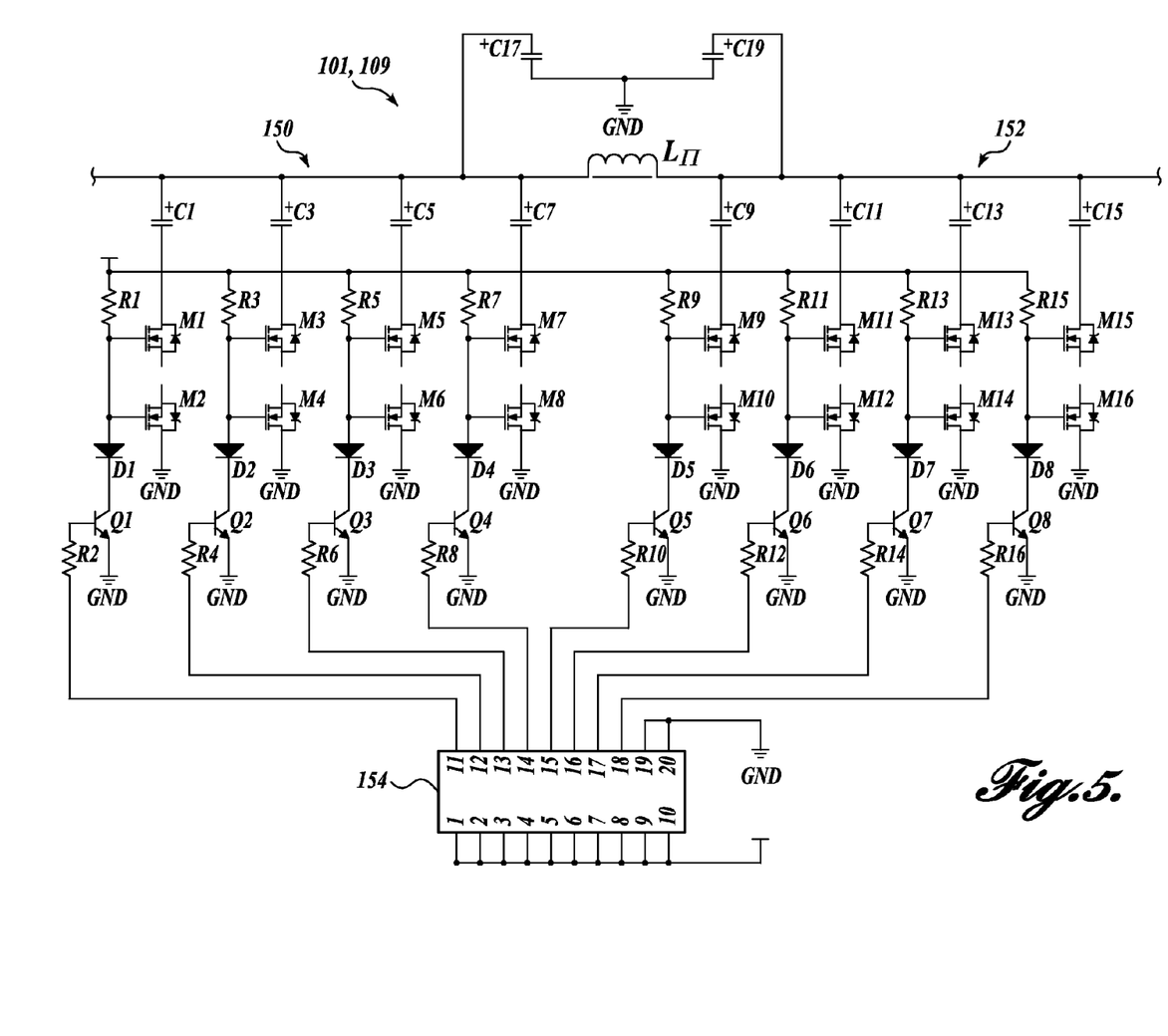
FIG. 5 is a circuit diagram for implementing a π-match network such as that shown in FIG. 4.

An exemplary circuit for implementing the first and/or second π-match networks 101, 109 is shown in FIG. 5. The variable capacitors $C_{S1}$, $C_{L1}$, $C_{L2}$ are implemented with a plurality of capacitors C1-C15 networked in switchable capacitor banks 150, 152. Each of the capacitors C1-C15 in the capacitor banks 150, 152 are selectively engagable. A microcontroller 154 is configured to engage the desired capacitors, which are selected to approximately maximize S21.

Although the current embodiment positions the π-match networks 101, 109 in line with the drive loop 103 and load loop 107, it is contemplated by the present invention that one or both of the drive loop 103 and load loop 107 may alternatively be replaced by the π-match networks 101, 109, respectively, with the corresponding inductor Lπ serving as the drive and/or load loop(s).

In practice, it may be time consuming to determine the optimal values using the algorithm illustrated in FIG. 4. In an alternative embodiment, using the capacitor banks shown in FIG. 5, a control algorithm may exhaustively sweep each possible combination of capacitor settings while monitoring one or more of the scatter parameters, and select the configuration that achieves minimum reflected power. For example, ten switchable shunt capacitors (five on each side of the inductor) have a topology with 1,024 possible states.

It is also contemplated, and will be apparent to persons of skill in the art, that other approximate methods may be selected to arrive at an optimal set of capacitor settings, in order to achieve more rapid switching in a dynamic environment. For example, the control algorithm may be configured to intelligently estimate the coupling coefficient between the two MCR coils, for example, by detecting the distance between the MCR coils 104, 106. A table of the optimal component values representing the possible physical arrangements between the two MCR coils 104, 106 may be pre-calculated, and the physical positioning of the MCR coils 104, 106 may be used with a lookup table to control the optimal capacitor bank 150, 152 settings.

In another embodiment, the received power may be monitored at the receive side of the system, and an out of band radio link may be used to report buck to the control algorithm at the transmit side the status of the received power. The system may then automatically detect a change in distance between the MCRs, and only conduct a sweep when a change in the coupling coefficient is detected. In another embodiment, the control algorithm may use a gradient approach to select only a subset of possible capacitor settings to find a local maximum transfer efficiency.

A significant challenge in developing effective wireless power systems is the efficient rectification of RF power to DC power across the system's operating points. This issue arises front the need to maintain optimal impedance matching between the receiving antenna and the rectifier while the load impedance of the application is changing.

To maintain optimal power transfer while undergoing changes in the coupling coefficient between the MCR coils 104, 106 (which is affected by the distance and orientation between the source and the load, and by fluctuations in the load), an adaptive rectifier has been developed that uses a nonlinear impedance matching circuit element and a custom control algorithm to adapt to changes in the environment.

Figure 6:
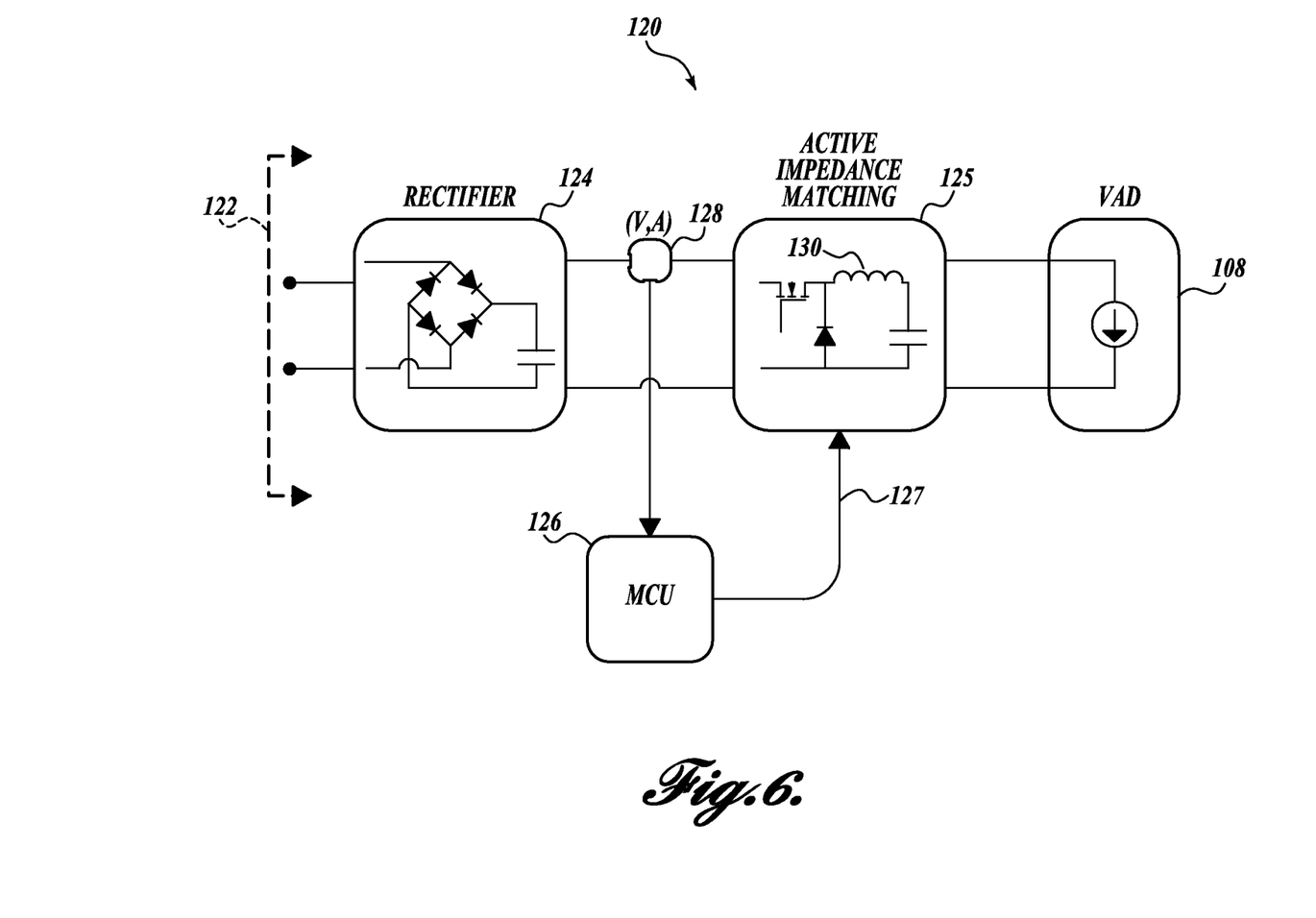
FIG. 6 is a diagram illustrating an adaptive rectifier system in accordance with the present invention.

A diagram of an adaptive rectifier system 120 is shown in FIG. 6. In this exemplary embodiment, RF power 122 from the Rx side second π-match network 109 (FIG. 4) is provided to a full wave rectifier 124 that converts the RF power 122 into direct current. A dynamic impedance matching circuit 125 is controlled by a microcontroller 126 that receives input from conventional voltage and current sensing circuits 128 and generates a pulse width modulated (PWM) control signal 127. A feed-forward buck converter 130 is used to control the ratio of voltage to current that is drawn from the rectifier 124 and delivered to the VAD 108. Additional control algorithms and/or voltage regulation stages may be provided for a particular application.

The adaptive rectifier system 120 architecture and the control algorithms implemented on the microcontroller 126 are similar to known Maximum Power Point Tracking (MPPT) techniques used for harvesting maximum power from solar cells. See, for example, U.S. Pat. No. 7,986,122, to Fornage et al., which is hereby incorporated by reference.

In a wireless power transfer system such as the system 100 described above (FIG. 4), the output of the MCR Rx coil 106 and the match network 109 presents a variable source resistance and the typical application will present a variable load resistance. Thus adaptation techniques are beneficial to optimize power transfer.

In a current prototype apparatus, the adaptive rectifier system 120 consists of a full bridge rectifier 124, over voltage protection (not shown), a high voltage synchronous NMOS driver (LTC4444), circuits for measuring voltage and current 128, and an MSP430 microcontroller 126 that implements the control algorithm for tracking the maximum power point of the rectifier 124. The prototype was designed for robustness and fault tolerance. Further optimization and size reduction are contemplated.

One commonly overlooked aspect of RF rectifier design is that the load impedance of the application is essentially transferred through the rectifier and impacts the impedance match between the RF antenna/coils and the input of the rectifier itself. Occasionally this apparent power loss to the load is interpreted as inefficiencies in the rectifier. However, the present inventors believe the apparent power loss is due to RF power being reflected off of the rectifier-antenna interface.

For example, consider an RF amplifier connected to an ideal rectifier that is terminated into a 200Ω load resistor. Since the rectifier is ideal, it will not alter the ratio of voltage to current (characteristic impedance) passing through it. The rectifier will simply invert the negative portion of the incoming sine wave. Thus, when looking into the rectifier, the impedance seen is simply that of the 200Ω resistor. Therefore, if the rectifier is driven by a source with a 50Ω characteristic impedance, a portion of the incident wave will be reflected off the mismatch between the 50Ω to 200Ω interface, resulting in apparent power loss to the load. For this example it is clear that the loading conditions placed on the rectifier make a significant impact on the total power delivered to the load.

To illustrate the issue of load matching and to demonstrate the effectiveness of the new adaptive rectifier and the improvement made when the adaptive rectifier is enabled, an experiment was performed wherein the RF amplifier 102 (FIG. 2) with a source impedance of 50Ω is connected to the adaptive rectifier 124. The RF amplifier 102 sweeps its output power from 3-30 watts at a fixed frequency of 13.56 MHz. At each sweep point, an electronic load provided a second sweep of load current, which emulated different power consumption modes that an application might present. The resulting rectifier 124 output voltages and currents were recorded using digital multimeters. A host computer running Labview® was used to control the system and record data.

When rectifier active impedance matching 125 is turned off, it was observed that under some loading conditions applied to the rectifier 124 an impedance mismatch occurs between the output of the coils and the input of the rectifier 124, and this mismatch results in poor power transfer. There is only a narrow ridge of points where maximum power transfer can be achieved.

When the active impedance matching circuit 125 is enabled, the MSP430 microcontroller 126 measures the output voltage and current ratio being delivered to the VAD 108. Its control algorithm adjusts the PWM signal 127 that drives the feed-forward buck converter 130. This maximizes rectified power and thus maximizes the amount of power delivered to the VAD 108. For nearly any input power level and load current, an operating point can be found that maximizes power transfer, which results in a plateau of near constant transfer efficiency. The conclusion is that rectifiers that use MPPT techniques can effectively mitigate load variation, which would normally disrupt power transfer.

The above disclosure describes a method for controlling the apparent load impedance seen by the output of the rectifier 124 to optimize the RF power transfer. In effect, the loading condition of the rectifier 124 maintains the optimal impedance match between the input of the rectifier 124 and the output of the RF amplifier 102.

Another way to look at the system 100 is that if the source impedance of the amplifier 102 (or magnetically coupled resonators) is not 50Ω, the maximum power point tracking algorithm on the microcontroller 126 will still servo the PWM control signal 127 to maximize the power transfer. This will, in turn, change the input impedance to the rectifier 124 to closely match the output impedance of the amplifier 102. Thus the active matching circuit block 125 can be used to control the real input impedance of the rectifier 124.

Controlling the duty cycle of the feed-forward buck converter 130 allows the adaptive rectifier to servo its input impedance. However, some reactance is introduced and the impedance matching is not purely real. This is believed to be due to the junction capacitance of the diodes. One possible improvement to the system, therefore, would be to mitigate this parasitic reactance with a switched impedance matching network. Ultimately, this shows that using a feed-forward buck converter 130 to form an adaptive rectifier is an effective means of electronically controlling the RF impedance of a rectifier 121 using only solid state devices.

Figure 7:
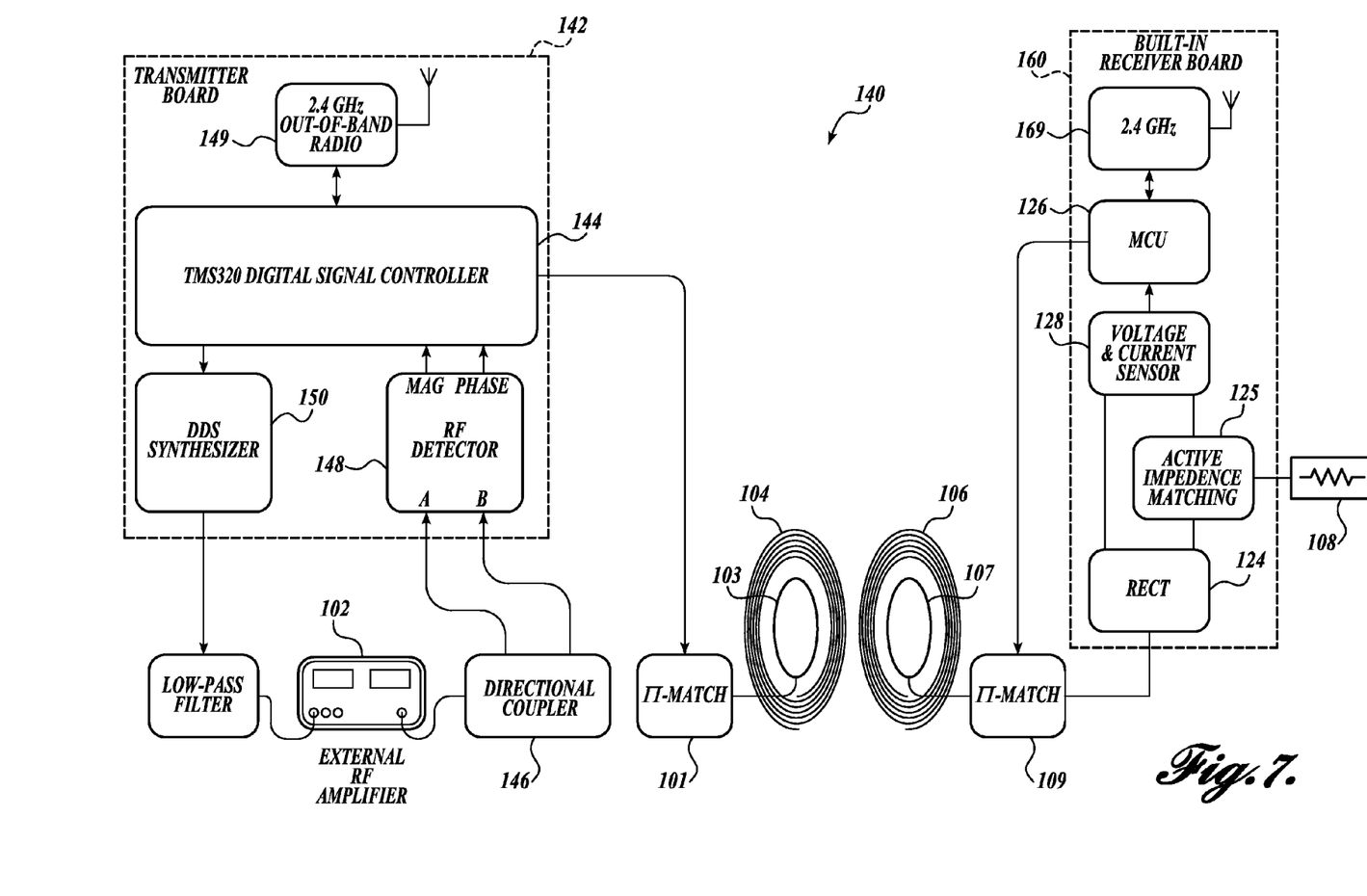
FIG. 7 is a block diagram illustrating another embodiment of a wireless power system in accordance with the present invention.

Another embodiment of a system 140 is shown schematically in FIG. 7. The system 140 includes a transmitter board 142 with a digital signal controller (DSC) 144, for example a TMS320® DSC 144. The DSC 144 controls all peripherals on the transmitter board 142 and communicates with an external PC via a serial-to-USB chip (not shown). To detect how much power the system delivers to the load 108, the incident and reflected ports of a directional coupler 146 are attached to the inputs of an RF detector chip 148. The detector chip 148 outputs a voltage that is proportional to the log magnitude ratio and phase between incident and reflected power (i.e., 1/S11). For example, if the DSC 144 is clocked at 150 MHz it may take many digital samples in a short period of time. In fact, it only takes this system 140 about 5 μs to obtain one data point.

Using these measurements, the DSC 144 adjusts the transmit frequency of an RF synthesizer 150, which drives the amplifier 102. Optionally, the system 140 may also employ dynamic impedance matching by controlling π-match boards 101, 109, for example, via parallel general purpose input/output ("GPIO") interfaces from the DSC 144. An external RF amplifier 102 is used to achieve an output power of up to 100 W in this exemplary embodiment. The receive side includes a receiver board 160 that contains a rectifier system 120. Optionally, both the transmitter board 142 and the receiver board 160 include CC2500 radios 149, 169, which implement out-of-band communication and allow the load to provide information about power consumption, position, or orientation, as well as control for a remote π-match board.

The system's 140 control algorithm chooses the optimal system parameters (π-match settings) given the current system state and maximizes power transfer over time as described above.

The system 140 is capable of fixed frequency operation using dynamic impedance matching. π-match boards 101, 109 contain capacitor banks that can be switched on or off by a parallel GPIO interface. The search space for π-match is more complicated than that of frequency tuning. Where frequency tuning's search space was one-dimensional, the space for impedance matching is two-dimensional, as the system can change both the Tx-side or Rx-side capacitances. Thus, the bank capacitor values should be chosen to provide the most effective matching circuit with the fewest number of capacitors. It is contemplated that for any given arrangement of MRC coils it may be determined that some capacitor settings will not correspond to optimal impedance matches, and may be excluded from the search space ahead of time.

Wireless power systems based on magnetically coupled resonators can realize the vision of seamless, reliable wireless power delivery if they are able to adapt to variations in range, orientation, and loading conditions. The key insight is that the over-coupled regime allows for high efficiency and near constant power delivery if the system is tuned properly.

In particular, we have demonstrated that adaptive impedance matching techniques used for fixed frequency operation can enable wireless power delivery to larger areas of space than previously published work. Additionally, we have introduced an adaptive rectifier topology that is capable of adapting to changes in loading conditions to allow for optimal power delivery to the load. Conversely, the adaptive rectification technique also allows a receiver to control its input impedance to ensure proper matching to the magnetically coupled resonators. Finally, a full end-to-end system capable of adapting to real-time changes in the environment while maintaining optimum efficiency is disclosed.

While illustrative embodiments have been illustrated and described, it will be appreciated that various changes can be made therein without departing from the spirit and scope of the invention.

What is claimed is:

1. A method for powering a medical device implanted in a subject, comprising:
    transmitting radio frequency energy from a power source to an external drive loop that is inductively coupled to an external transmitter resonator; and
    magnetically coupling the external transmitter resonator to an implanted receiver resonator that is coupled to a medical device implanted in a subject, such that power is transferred to the implanted medical device;
    wherein the magnetic coupling further includes an external relay resonator.

2. The method of claim 1, further comprising providing a garment wearable by the subject, wherein the garment has the relay resonator integrated therewith.

3. The method of claim 1, further comprising adjusting an impedance of the magnetically coupled resonators.

4. The method of claim 3, further comprising monitoring the drive loop with a sensor to determine if the impedance should be adjusted.

5. A system for powering an implantable medical device, comprising:
    at least one external subsystem comprising a drive loop, a power source, and a transmitter resonator, wherein the drive loop is inductively coupled to the transmitter resonator when the power source provides radio frequency energy to the drive loop;
    an implantable subsystem comprising a receiver resonator, a load loop, and a medical device, wherein the load loop is inductively coupled to the receiver resonator and operably connected to the medical device;
    wherein the transmitter resonator and the receiver resonator are configured to form a magnetic coupling to complete transfer of power from the at least one external subsystem to the implantable subsystem to deliver power from the power source to the medical device,
    wherein the system further comprises a relay resonator, and
    wherein the relay resonator forms part of the magnetic coupling.

6. The system of claim 5, wherein the relay resonator is integrated in a garment.

7. The system of claim 5, wherein the at least one external subsystem comprises a plurality of external subsystems, wherein the plurality of external subsystems are distributed within a defined space, and further wherein the receiver resonator is configured to selectively receive energy from one or more of the plurality of external subsystems disposed within the defined space.

8. The system of claim 7, wherein the receiver resonator is configured to receive energy from a nearest one of the plurality of external subsystems.

9. The system of claim 7, further comprising a plurality of relay resonators disposed within the defined space.

10. The system of claim 9, wherein the plurality of external subsystems and the plurality of relay resonators are distributed such that during use the receiver resonator in the implantable subsystem will form a magnetic coupling with at least one of the transmitter resonators from anywhere within the defined space.

11. The system of claim 5, wherein the at least one external subsystem comprises a portable energy system comprising an energy source and a portable transmitter resonator, wherein the portable energy system is operable to selectively couple the portable transmitter resonator with the receiver resonator through the relay resonator to form a magnetic coupling such that the portable energy system provides power to the medical device.

12. The system of claim 5, wherein the at least one external subsystem comprises a sensor operable to monitor the drive loop; and wherein the system further comprises a controller operable to receive data from the sensor, and to use the received data to actively control the system to optimize energy transfer efficiency.

13. The system of claim 12, wherein the sensor comprises a directional coupler.

14. The system of claim 12, wherein the controller controls the power source output frequency to optimize energy transfer efficiency.

15. The system of claim 12, wherein the at least one external subsystem further comprises a matching network that is operably connected to the drive loop, and further wherein the controller controls the matching network to change the impedance of the system to optimize energy transfer efficiency.

16. The system of claim 15, wherein the matching network comprises at least one of the group consisting of a n-match network and an L-match network.

17. The system of claim 15, wherein the implantable subsystem further comprises a second matching network that is operably connected to the load loop.

18. A system for powering an implantable medical device, comprising:
    at least one external subsystem comprising a drive loop, a power source, and a transmitter resonator, wherein the drive loop is inductively coupled to the transmitter resonator when the power source provides radio frequency energy to the drive loop;
    an implantable subsystem comprising a receiver resonator and a medical device, wherein the receiver resonator is operably connected to the medical device;
    wherein the transmitter resonator and the receiver resonator are configured to form a magnetic coupling to complete transfer of power from the at least one external subsystem to the implantable subsystem to deliver power from the power source to the medical device,
    wherein the system further comprises a relay resonator, and
    wherein the relay resonator forms part of the magnetic coupling.

* * * * *